United States Patent [19]

Cover et al.

[11] Patent Number: 5,250,435

[45] Date of Patent: Oct. 5, 1993

[54] **MUTANT STRAINS OF *ASPERGILLUS TERREUS* FOR PRODUCING 7-[1,2,6,7,8,8A(R)-HEXA-HYDRO-2(S),6(R)-DIMETHYL-8(S)-HYDROXY-1(S)-NAPHTHYL]-3(R),5(R)-DIHYDROXYHEPTANOIC ACID (TRIOL ACID),I)**

[75] Inventors: William H. Cover, Lansdale, Pa.; Rebecca L. Dabora, Andover, Mass.; Anderson Hong, Taipei, Taiwan; Christopher Reeves, Mill Creek, Wash.; Robert W. Stieber, Harrisonburg; Victor A. Vinci, Charlottesville, both of Va.

[73] Assignee: Merck & Co., Inc., Rahway, N.J.

[21] Appl. No.: 709,950

[22] Filed: Jun. 4, 1991

[51] Int. Cl.$^5$ .................. C12P 7/42; C12P 17/06; C12N 1/14; C07D 305/00
[52] U.S. Cl. ................... 435/256.1; 435/125; 435/146; 435/913; 549/214; 549/292; 514/460
[58] Field of Search ............... 435/125; 424/279; 549/214

[56] References Cited

U.S. PATENT DOCUMENTS

| | | | |
|---|---|---|---|
| 4,231,938 | 11/1980 | Monaghan et al. | 435/125 |
| 4,444,784 | 4/1984 | Hoffman et al. | 424/279 |
| 4,876,364 | 8/1989 | Schuda et al. | 549/214 |
| 4,916,239 | 4/1990 | Treiber | 549/292 |

FOREIGN PATENT DOCUMENTS

| | | | |
|---|---|---|---|
| 0033537 | 8/1981 | European Pat. Off. | 435/125 |
| 2479809 | 4/1981 | France. | |
| 61-13798 | 4/1986 | Japan. | |

OTHER PUBLICATIONS

Nakamura et al. Isolation & Biosynthesis of 3αhydroxy-3,5-hihydromonacolin L, The Journal of Antibiotics 43(12) 1990 pp. 1597-1600.
M-S Shiao et al., *Proc. Nat'l Sci. Counc. B. Roc*, 11:223-231 (1987).
Endo et al., *J. Antibiotics*, 39 1670 (1989).

*Primary Examiner*—David M. Naff
*Assistant Examiner*—Deborah Hung
*Attorney, Agent, or Firm*—Joseph DiPrima; Melvin Winokur

[57] ABSTRACT

Novel strains of *Aspergillus terreus* have been discovered which provide fermentation production of at least 5.2 g/L of 7-[1,2,6,7,8,8a(R)-hexahydro-2(S),6(R)-dimethyl-8(S)-hydroxy-1(S)-naphthyl]-3(R),5(R)-dihydroxyheptanoic acid (triol acid, I), but with production of not more than 0.85 g/L of (triol acid)-related side products and specifically less than 0.10 mg/liter of lovastatin. The predominant fermentation product triol acid, may be converted in a straightforward manner to its lactone form, in which it is an inhibitor of HMG-CoA reductase and thus useful as an antihypercholesterolemic agent, and in which it may also serve as an intermediate for preparation of other HMG-CoA reductase inhibitors.

4 Claims, No Drawings

MUTANT STRAINS OF ASPERGILLUS TERREUS FOR PRODUCING 7-[1,2,6,7,8,8A(R)-HEXA-HYDRO-2(S),6(R)-DIMETHYL-8(S)-HYDROXY-1(S)-NAPHTHYL]-3(R),5(R)-DIHYDROXYHEPTANOIC ACID (TRIOL ACID),I)

BRIEF SUMMARY OF THE INVENTION

The present invention relates to strains of *Aspergillus terreus* useful in a novel fermentation process for the production of at least 5.2 g/L of 7-[1,2,6,7,8,8a(R)-hexahydro-2(S),6(R)-dimethyl-8(S)-hydroxy-1(S)-naphthyl]-3(R),5(R)-dihydroxyheptanoic acid (troil acid, I) by mutant strains of *Aspergillus terreus*, with production of 0.85 g/L or less of triol acid-related side products, as those are defined further below and less than 0.10 mg/liter of lovastatin.

Triol acid (I) is an inhibitor of 3-hydroxy-3-methylglutaryl-coenzyme A (HMG-CoA) reductase, an enzyme involved in cholesterol biosynthesis. As an inhibitor of that enzyme, the triol acid is useful as an antihypercholesterolemic agent. It finds further usefulness as an intermediate for the preparation of other antihypercholesterolemic agents, especially those having various side chains at the 8-position of the polyhydronaphthyl ring. For example, simvastatin, which has a 2,2-dimethylbutyryloxy side chain at that position, may be prepared using the lactone form of the triol acid as a starting material, in accordance with procedures described in U.S. Pat. No. 4,444,784.

The present invention specifically relates to the strain MF-5544 of *Aspergillus terreus*, ATCC 74064 and to mutant strains thereof which are capable of producing at least 5.2 g/L of triol acid (I) and not more than 0.85 g/L of (triol acid)-related side products and less than 0.10 mg/liter of lovastatin.

The present invention also relates to a fermentation process in which the herein disclosed strains of *Aspergillus terreus* are grown in the presence of a culture medium to produce the triol acid as the predominant fermentation product.

BACKGROUND OF THE INVENTION hypercholesterolemia is known to be one of the prime risk factors for atherosclerosis and coronary heart disease, the leading cause of death and disability in western countries. Bile acid sequestrants seem to be moderately effective as antihypercholesterolemic agents but they must be consumed in large quantites, i.e., several grams at a time, and they are not very palatable.

MEVACOR® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof. For example, simvastatin wherein the 8-acyl moiety is 2,2-dimethylbutyryloxy is an even more potent HMBG-CoA reductase inhibitor than lovastatin. Simvastatin is now commercially available as ZOCOR® in some markets.

The triol acid (I), produced by the process disclosed herein, may after lactonization to its corresponding diol lactone (II), serve as a starting material for the formation of simvastatin and other 8-ester analogs and derivatives containing the polyhydronaphthyl moiety and which function as HMG-CoA reductase inhibitors.

The diol lactone (II) noted above has been produced by fermentation of *Monascus ruber* as described by Endo et al, published Japanese Patent Appln. 86-13798 (1986). A more recent publication by Endo, *J. Antibiotics*, 39, 1670 (1989) discloses various strains of *Monascus ruber* which yield mevinolin (lovastatin) and triol acid (I). Furthermore triol acid (I) and its corresponding diol lactone (II) have been produced by chemical hydrolysis of the 8-(α-methylbutyryloxy) group from lovastatin.

However, there is no teaching or suggestion in the art for the production of triol acid (I) employing a culture of *Aspergillus terreus* and forming the triol acid in high yield with a minimum production of triol acid related side products. Indeed there is no teaching or suggestion in the prior art that triol acid (I) can be formed, by any microbe, in high yield with a minimum production of triol acid related side products. As noted it is a significant advantage of the present invention that these, difficult to separate, triol acid related side products are formed in very low amounts.

DETAILED DESCRIPTION OF THE INVENTION

The present invention relates to a novel fermentation production of 7-[1,2,6,7,8,8a(R)-hexahydro-2(S),6(R)-dimethyl-8(S)-hydroxy-1(S)-naphthyl]-3(R),5(R)-dihydroxyheptanoic acid (triol acid, I), which employs a culture of *Aspergillus terreus*. The triol acid (I) may be further converted under lactonization conditions to its corresponding diol lactone (II).

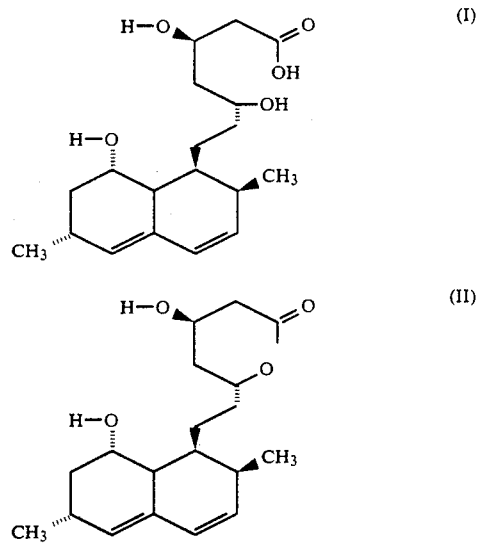

The present invention concerns novel strains of *Aspergillus terreus* which have been found to produce significant quantities of triol acid (I), a surprising discovery in light of the fact that *Aspergillus terreus* has been known heretofore to produce only compounds having 8-position ester side chains.

The novel strains of *Aspergillus terreus* included in the present invention are characterized by the fact that they are able to produce at least 5.2 g/L of the triol acid (I) but not more than 1 g/L of triol acid-related side products, and specifically less than 0.10 mg/liter (<0.002%) of lovastatin.

The term "triol acid-related side products" is defined herein to mean any HMG-CoA reductase inhibitor, other than (I) and (II), of the polyhydronaphthyl structure which exhibits a UV spectrum of $\lambda max = 238$ nm due to the conjugated decene ring system. The fact that the present novel strains of *Aspergillus terreus* included within this invention produce high yields of triol acid and low amounts of triol acid related side products, and specifically no lovastatin (<0.002%), is unexpected and surprising in light of the prior art in this area.

The triol acid-related side products are close in structure to the triol acid itself and thus are difficult to separate from the triol acid which is the product of interest. It is a significant advantage of the present invention that these triol acid related side products are formed in very low amounts.

The novel strains of *Aspergillus terreus* included within the present invention can be obtained by mutagenesis of lovastatin producing strains of *Aspergillus terreus* which are publicly available. For example, U.S. Pat. No. 4,231,938 describes lovastatin-producing strain MF-4833, which is deposited with the American Type Culture Collection under accession No. ATCC 20541. Such a strain may be subjected to mutagenesis, e.g., by treatment with UV, nitrosoguanidine and psoralen-crosslinking mutagenesis. The extent of mutagenesis may be determined by auxotrophy, i.e., the requirement of the mutated strain for a specific growth substance beyond the minimum required for normal metabolism and reproduction by the parent strain. An alternative monitoring system involves use of the intercalating dye acriflavine, which prevents any growth of the parent lovastatin-producing strains when plated at $10^5$ spores per plate but, following mutagenesis, allows growth of about 3-5 colonies per plate. Mutant strains are reisolated and pooled and subjected to further mutagenesis so that, by repetition of these procedures, mutated strains of *Aspergillus terreus* can be obtained which fall within the definition of those to which the present invention relates.

The usual aim is for mild mutagenesis to avoid accumulating too many deleterious mutations in the parent strains. However, the triol producing strain MF-5544 mutant was isolated after relatively heavy mutagenesis with nitrosoguanidine, a powerful mutagen.

Employing the above mutagenesis procudure and the detailed description of Example 1 it is possible to produce strains of *Aspergillus terreus* which yield high titers of triol acid (I), but no detectable amount of lovastatin (less than 0.10 mg/L), and less than 0.85 g/L of triol acid-related compounds.

*Aspergillus terreus*, MF-5544, produces up to 5.95 g/L triol acid in 14 days. Small amounts (less than 0.85 g/L) of a triol-related compound are produced also; but there is no production of lovastatin (less than 0.10 mg/L). The above mutagenesis procedure and accompaning Examples provides a fully enabling route to the formation of triol acid (I). The particular strain MF-5544 has been deposited with the American Type Culture Collection, under the Budapest Treaty as ATCC 74064. This deposit has been carried out to provide the best mode for conducting the present invention. The strain *Aspergillus terreus*, MF-5544 exhibits the following morphological features:

Colonies attaining a diameter of 10 mm on yeast-malt extract agar (Difco) at 20° C. 12/12 hr light/dark in 7 days; attaining a diameter of 34 mm on the same medium at 37° C. in 7 days; attaining a diameter of 12 mm on oatmeal agar (Difco) at 20° C.; attaining a diameter of 45 mm on oatmeal agar (Difco) at 37° C. Colonies distinctly radially plicate or folded at 37° C., compared to growth at 20° C. On yeast-malt extract agar at 20° C., colonies up to 0.5 mm deep, slightly raised, velutinous to slightly floccose, dull, margin submerged, entire, hyaline to pale yellowish buff or pale pinkish buff, Light Buff, Pale Ochraceous-Buff, Pale Pinkish Cinnamon (capitalized color names from Ridgway, R. 1912. Color Standards and Nomenclature, Washington, D.C.) at the margin, soon pinkish buff to pinkish brown, Pinkish Buff, Light Pinkish Cinnamon, Buff-Pink, Cinnamon-Buff, finally dull pinkish tan, Pinkish Cinnamon, Cinnamon, Clay Color, reverse dull yellow gray to cream-yellow, Cream Color, Light Buff, Warm Buff at the margin, but soon yellow to ochraceous, Colonial Buff, Deep Colonial Buff, Chamois, Yellow Ocher, with a yellow diffusible pigmented exuded from the edges of the colony a few mm into the agar.

Conidiophores arising from foot cells, 120-190 $\mu$m tall, 4.5-6.5 $\mu$m wide, straight or flexuous, sometimes with irregular constrictions, often slightly constricted just below the vesicle, thick-walled, with walls approximately 0.5 $\mu$m thick, smooth, hyaline. Conidial heads 50-100 $\mu$m in diameter at the apex of the conidial column, biseriate with groups of conidiogenous cells arising from metulae, columnar, with conidial chains slightly splitting in age, a first white but soon becoming pale pink, uniformly pinkish buff at maturity. Conidogeneous cells phialidic, arising from metulae in groups of 1-5, usually 3-4, 5-10 1.5-3 $\mu$m, cylindrical, with distal end tapered or with a slightly flared collarette. Metulae broadly cylindrical to subclavate, with peripheral metulae curved upward, 6-10×2.5-4.5 $\mu$m. Vesicles 10-26 $\mu$m in diameter, subglobose to hemispherical with metulae covering the upper 40-60%. Conidia 1.5-4 $\mu$m in diameter, globose to subglobose, smooth, hyaline in KOH, adhering in chains by colorless connectives. Hyphae septate, smooth, highly branched, up to 10 $\mu$m in diameter, with thicker hyphae containing highly refractive content, with older submerged hyphae producing lateral and terminal chlamydospores ("aleurospores"). Chlamydospores produced blastically, abundant, 6-10 $\mu$m in diameter, globose to subglobose, hyaline, with refractive contents. Hulle cells, sclerotia, and cleistothecia absent.

CULTURE MEDIUM

The fermentation of the mutant strains of *Aspergillus terreus* included within the present invention is carried out in aqueous media such as those employed for the production of other fermentation products. Such media contain sources of carbon, nitrogen and inorganic salts assimilable by the microorganism.

In general, carbohydrates such as sugars, for example, lactose, glucose, fructose, maltose, sucrose, xylose, mannitol and the like and starches such as grains, for example, oats, ryes, cornstarch, corn meal and the like can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 18% and 35% by weight of the medium. These carbon sources can be used individually, or several such carbon sources may be combined in the medium. In general many proteinaceous materials may be used as nitrogen sources in the fermentation process. Suitable nitrogen sources include for example, yeast hydrolysates, primary yeast, soybean meal, cottonseed flour, hydrolysates of casein, corn steep liquor, distiller's solubles or tomato paste and the like. The sources of nitrogen either alone or in combination, are used in amounts ranging from about 5% to 60% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the media described in the Examples are merely illustrative of the wide variety of media which may be employed and are not intended to be limitative. Specifically, the carbon sources used in the culture media to produce triol acid may include dextrose, dextrin, oat flour, oatmeal, molasses, citrate, soybean oil, glycerol, malt extract, cod liver oil, starch, ethanol, figs, sodium ascorbate and lard oil. Included as nitrogen sources are peptonized milk, autolyzed yeast, yeast RNA, tomato paste, casein, primary yeast, peanut meal, distillers solubles, corn steep liquor, soybean meal, corn meal, NZ amine, beef extract, aspargine, cottonseed meal and ammonium sulfate. The major ionic components are $CaCO_3$, $KH_2PO_4$, $MgSO_4.7H_2O$ and NaCl and small amounts of $CoCl_2.6H_2O$ and traces of Mn, Mo, B and Cu may also be present.

The ingredients are added to a 1 liter flask and the volume brought to 1 liter with distilled water. The pH is adjusted to 7.0 with 40% NaOH while the medium is continuously stirred, and the pH is allowed to stabilize for 15 minutes. The culture medium is dispensed in 30 ml aliquots into non-baffled 250 ml flasks, in which it is autoclaved for 20 minutes at 121° C. These flasks are then ready inoculated with the seed inoculum described in Example 1.

FERMENTATION PROCESS AND CONDITIONS

In a preferred embodiment, the fermentation is carried out at temperatures ranging from about 20° to 37° C.; however for optimum results it is preferable to conduct the fermentation at temperatures of from about 22° to 30° C. The pH of the nutrient media suitable for growing the Aspergillus culture and producing triol acid can vary from about 6.0 to 8.0.

Although the triol acid is produced by both surface and submerged culture, it is preferred to carry out the fermentation in the submerged state. A small-scale fermentation is conveniently carried out by inoculating a suitable nutrient medium with Aspergillus culture and, after transfer to a production medium, permitting the fermentation to proceed at a constant temperature of about 28° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 28° C. for 2 days, or until growth is satisfactory, and some of the resulting growth is used to inoculate either a second stage seed or the production medium. Intermediate stage seed flasks, when used, are developed in essentially the same manner, that is, part of the contents of the flask from the last seed stage are used to inoculate the production medium. The inoculated flasks are shaken at a constant temperature for several days, and at the end of the incubation period the contents of the flasks are centrifuged or filtered.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of time as, for example, from 3 to 16 days while agitating and/or aerating the nutrient medium and maintaining the temperature at about 28° C. This method of producing the triol acid is particularly suited for the preparation of large quantities.

ISOLATION OF FERMENTATION PRODUCT

Triol acid is present in the fermentation broth largely in the hydroxycarboxylate (open lactone) form. In a preferred procedure, whole broth extraction of MF-5544 fermentations is carried out using similar practices for lovastatin whole broth extraction (U.S. Pat. No. 4,231,938).

Analysis of HPLC traces indicated that most of the contaminating species present in whole broth were removed in an initial isopropyl acetate (IPAc) extraction after pH adjustment to 3.5–4.5 while 70–72% of the triol was recovered at this step. This was followed by a carbonate extraction (pH 11–12) with a very low loss of triol acid (<0.5%). A final IPAC extraction (pH 3.5–4.5) of the rich carbonate layer is conducted to recover the triol acid in an organic phase with very little reduction in yield.

LACTONIZATION

Fermentation of *Aspergillus terreus* strains in accordance with the process of the present invention provides the triol acid as the predominant product. Lactonization of triol acid is carried out using standard procedures, i.e., either heat or acid catalyzed lactonization. A procedure for acid-catalyzed lactonization of lovastatin-related compounds is described in U.S. Pat. No. 4,916,239.

EXAMPLE 1

Preparation of
7-[1,2,6,7,8,8a(R)-hexahydro-2(S)-6(R)-dimethyl-8(S)-hydroxy-1(S)-naphthyl]-3(R),5(R)-dihydroxyheptanoic acid (Triol Acid I)

(a) Nitrosoguanide Mutagenesis & HPLC Assay

Mutagenesis:
1) A pure culture of a lovastatin producing strain of *Aspergillus terreus* was streaked onto slants of YME+TE and grown at 28° C. with typical room fluorescent lighting left on.
2) After 5 to 7 days, 2 milliliters of sterile storage solution (5% lactose, 10% glycerol, 0.005% NP-40) was added to each slant and the surface was gently rubbed with a sterile loop to release the conidiaspores.
3) The spore suspension was transferred to a screw cap tube containing about 25 sterile 0.5 mm glass beads and vortexed for about one minute. The spores were counted on a hemocytometer and diluted to $1 \times 10^8$ spores/ml in storage solution. Spore suspensions were stored at −80° C. until ready to use.
4) Four one ml aliquots of the above spore suspension were placed in snap-cap microfuge tubes and centrifuged at 3000 g for 5 minutes a 4° C. The supernatant was discarded and each spore pellet was resuspended in 0.9 ml phosphate buffer (100 mM sodium phosphate, pH 7, 0.005% NP-40) by vortexing.

5) To three of the tubes, 0.1 ml of 1 mg/ml N-methyl-N-nitroso-N'-nitroguanidine was added; 0.1 ml of water was added to the fourth. After mixing, the tubes were incubated at 28° C. The control was centrifuged immediately at 3000 g for 5 minutes at 4° C. The other three tubes were likewise centrifuged at 15, 30 and 60 minutes, respectively. Immediately after each centrifugation, the supernatant was discarded and the spores were resuspeneded in 1 ml of the above phosphate buffer.

6) Each tube of spores was diluted in water $1:10^4$, $1:10^5$ and $1:10^6$. Fifty μl of each dilution was plated onto several YME+TE plates (25 ml per 100 mm plate) and the plates were incubated at 28° C. under ambient fluorescent lights. After 4 days the colonies were counted (for plates that had a countable number).

7) After 2 more days individual colonies were picked from plates for which the spores had been mutagenized such that only 10% to 50% of the original spores had survived. Picked colonies were used to inoculate YME+TE slants which were grown as above.

8) When the slants containing the selected mutants had sporulated, spore suspensions were prepared as above and used to inoculate seed media ($5 \times 10^6$ spores/ml media; 40 ml in 250 ml unbaffled flasks). After 28 hours, the seed was inoculated into fermentation media (10% crossing volume; 30 ml fermentation media in 250 ml unbaffled flasks). All flasks were shaken at 220 rpm on a New Brunswick G-53 shaker at 28° C.

9) After 8 days of fermentation, one volume of methanol was added to each flask, flasks were agitated for 30 minutes, the contents was allowed to settle, and the supernatant was assayed by HPLC for the presence of triol and other broth components.

HPLC Assay of Culture Extracts

Extracts were analyzed by HPLC under isocratic mobile phase conditions of 45% acetonitrile and 55% 0.1% phosphoric acid pumped at 1.5 mls/minuted throught a Whatman Partisil 5 C8 (4.6 mm×25 cm) column. Detection wavelength was 235 nm. Triol producers were identified by their characteristic UV spectrum and by retention time in comparison with a triol ammonium salt standard.

b) Preparation of Slant Cultures

The culture, *Aspergillus terreus*, MF-5544 was maintained by culturing on agar slants containing YME+TE medium (8 mls) in capped glass tubes. The culture was grown on slants for 5-7 days at 27.5° C. and was stored for up to 1 month at 4° C; the slants were used as a source of inoculum for seed flasks. The YME+TE medium has the following composition:

| YME + TE Medium (Agar Slants): | |
|---|---|
| Yeast Extract | 4.0 g/L |
| Malt Extract | 10.0 g/L |
| Glucose | 4.0 g/L |
| Trace Elements #2 | 5.0 g/L |
| Agar | 20.0 g/L |
| Adjust to PH 7.0 with NaOH. Autoclave 20 min., 121° C. | |
| Trace Elements #2 | |

| -continued | |
|---|---|
| YME + TE Medium (Agar Slants): | |
| $FeSO_4.7H_2O$ | 1000 mg/L |
| $MnSO_4.H_2O$ | 1000 mg/L |
| $CuCl_2.H_2O$ | 25 mg/L |
| $CaCl_2$ | 100 mg/L |
| $H_3BO_3$ | 56 mg/L |
| $(NH_4)_6Mo_7O_{24}.4H_2O$ | 19 mg/L |
| $ZnSO_4.7H_2O$ | 200 mg/L |
| Prepare in 0.6N HCl, store at 5° C. | |

The highest titers were obtained using a seed inoculum which was grown in an "HLC" seed medium having the following components:

| "HLC" Medium | |
|---|---|
| Component | g/L |
| $KH_2PO_4$ | 15 |
| Cerelose | 20 |
| Ardamine pH | 1 |
| Pharmamedia | 15 |
| Lactic acid (88%) | 2 |
| Ammonium citrate | 4 |

Ardamine pH is available from Champlain Industries and is a blended yeast-primary grown, and brewer's yeast.

Pharmamedia was purchased from Trader's Protein Company and is "cottonseed flour".

Each of the above ingredients was added sequentially to distilled water, allowing each to dissolve before adding the next. 800 ml of distilled water was added to achieve a final volume of 1000 ml, and the pH was adjusted to 7.0 with 40% NaOH, allowing 10 minutes for stabilization. The medium was autoclaved for 20 minutes at 121° C. The post sterile pH should be 6.5-6.6.

c) Production Via Fermentation

To prepare inoculum for seed flasks, the contents of 1 agar slant was scraped with 5 ml distilled water or saline (0.7% NaCl). One ml of this inoculum was added to a 250 ml unbaffled Erlenmeyer flask containing 40 ml HLC seed medium which had been sterilized by autoclave. (Alternatively, 1 ml of lactose/glycerol spore suspension can be used as in example 2). The HLC seed flask was incubated at 27.5° C. for 24-26 hrs on a rotary shaker at 220 rpm; one ml from the contents of this flask was inoculated into a 250 ml unbaffled Erlenmeyer flask containing 30 mls sterilized GP-9 production medium (see below). This flask was incubated for 4-14 days at 27.5° C. on a rotary shaker at 220 rpm. Maximal triol acid production was seen at 14 days.

| GP-9 Medium | |
|---|---|
| Component | g/L |
| Ammonium Citrate | 9 |
| Ardamine pH | 1.2 |
| Cerelose | 12 |
| Pharmamedia | 40 |
| Lactose | 245 |
| P200 | 2 ml |
| Pre-Sterile pH | 7.0 | d) Extraction of Triol acid

The triol was recovered from fermentation broth (2L; initially 5.98 g/L by HPLC analysis) by liquid-liquid extraction using isopropyl acetate (IPAC) as follows: The pH of the broth was adjusted to 4.0–4.5 using 10% sulfuric acid (60 mL) and the broth was mixed with IPAC (1:34 L) and centrifuged. The IPAC layer was recovered and mixed with a sodium carbonate solution of pH 11.5 (400 mL) to remove nonpolar components. The rich carbonate layer (now containing the triol) was then back extracted into IPAC (450 mL) after pH adjustment to 4.0 using 85% phosphoric acid (12 mL).

e) Lactonization

70% Methanesulfonic acid (MSA) (87 uL; 2 mM) was added to the IPAC layer of Example 1(d) and the solution was concentrated by evaporation to ~one-fifth of its original volume (100 mL). After the concentration/lactonization was complete by HPLC analysis, the IPAC was mixed with a sodium carbonate solution (100 mL) to remove any charged species. The diol lactone crystallized out of the IPAC layer at −20° Celsius.

EXAMPLE 2

Preparation of Frozen Conidia From Rice

*Aspergillus terreus* MF-5544 culture can be maintained as a frozen spore suspension. 250 gm of "Uncle Ben's Converted Long Grain Rice" was washed with water in a 2800 ml Erlenmeyer flask until the water was clear. The water was drained from the flask, and the flask sterilized by autoclaving at 121° C. for 30 min. After cooling, the rice-containing flask was inoculated with the contents of 1 slant (suspended in 5 ml distilled water or saline (0.7% NaCl) by scraping), shaken, and allowed to incubate at 27.5° C. for 12-16 days. To recover spores, 250-500 mls of a solution containing 5% lactose/10% glycerol was added, the flask shaken, and the filtrate collected through a sterile stainless steel mesh. The lactose/glycerol spore suspension was frozen at −90° C. and used as a source of inoculum for HLC seed flasks as described above in Example 1.

EXAMPLE 3

Formation of Ammonium Salt

Cell pellets and/or cell debris were removed from the production flask by filtration or centrifugation. The filtrate or supernatant from this process was then extracted as indicated in Step 1d or the filtrate was used to isolate the ammonium salt of triol acid.

The IPAC stream (5 mL) with an estimated triol titer of 29.83 g/L) was dried over magnesium sulfate and then filtered through a sintered glass funnel. Methanol (0.2 mL) was added and the mixture was placed in an ice bath (0 celsius) and 0.03 mL of ammonium hydroxide:methanol (1:3) solution was added. The mixture was seeded with 1 mg of triol ammonium salt and aged for 30 minutes. The temperature was decreased to −8 Celsius and 0.03 mL of ammonium hydroxide:methanol (1:3) was added every 15 minutes for 2 hours. The resulting thick slurry was filtered to give ivory crystals.

A culture of a strain of *Aspergillus terreus* as claimed herein is defined as free of viable contaminating microorganisms which would be deleterious to the formation of a compound of formula (I).

What is claimed is:

1. A culture of a mutant strain of *Aspergillus terreus* wherein said strain is formed from the mutagenesis of a lovastatin producing strain of *Aspergillus terreus*, and wherein said mutant culture is capable of forming a compound of structure:

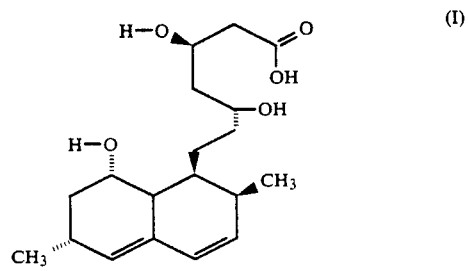

(I)

with the formation of less than 0.002% yield of lovastatin under culture conditions.

2. A culture of *Aspergillus terreus* MF-5544, ATCC 74064, or a mutant thereof, each capable of forming a compound of structure (I).

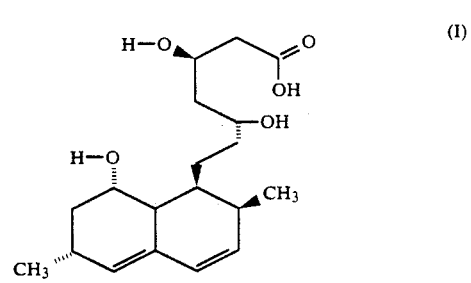

(I)

with formation of less than 0.002% yield of lovastatin.

3. A culture of claim 1 wherein the culture is a biologically pure culture.

4. A culture of claim 2 wherein the culture is a biologically pure culture.

* * * * *